United States Patent [19]

Come

[11] Patent Number: 5,124,134
[45] Date of Patent: Jun. 23, 1992

[54] APPARATUS FOR THE CONVERSION OF HYDROCARBONS

[75] Inventor: Guy M. Come, Nancy, France

[73] Assignee: Gaz de France, Paris, France

[21] Appl. No.: 506,350

[22] Filed: Apr. 9, 1990

Related U.S. Application Data

[62] Division of Ser. No. 278,521, Dec. 1, 1988, Pat. No. 4,952,743.

Foreign Application Priority Data

Dec. 3, 1987 [FR] France .................. 87 16804

[51] Int. Cl.$^5$ .......................... F27D 7/02; F27D 9/00; F27D 13/00
[52] U.S. Cl. .................................. 422/194; 422/202; 422/203; 422/205; 422/207; 431/167; 431/243
[58] Field of Search ............... 422/151, 156, 194, 202, 422/205, 207, 203, 167; 585/540, 541, 943; 431/242, 243, 190, 167

[56] References Cited

U.S. PATENT DOCUMENTS

| | | | |
|---|---|---|---|
| 2,512,586 | 6/1950 | Stengel | 422/203 X |
| 2,679,542 | 5/1954 | Dorsey et al. | 585/541 |
| 2,945,074 | 7/1960 | Elliott et al. | 585/540 |
| 3,047,371 | 7/1962 | Krause et al. | 422/207 X |
| 3,287,434 | 11/1966 | Stanton et al. | 585/540 |
| 3,366,460 | 1/1968 | Christensen | 422/203 |
| 3,753,662 | 8/1973 | Pagani et al. | 422/203 X |
| 4,014,654 | 3/1977 | Howell | 422/156 |
| 4,288,408 | 9/1981 | Guth et al. | 422/156 X |
| 4,360,497 | 11/1982 | Gasperson | 422/156 |
| 4,927,607 | 5/1990 | Berg | 422/151 X |

Primary Examiner—Robert J. Warden
Assistant Examiner—Amelia L. Santiago
Attorney, Agent, or Firm—Pollock, Vande Sande & Priddy

[57] ABSTRACT

The invention relates to a process and to an apparatus for the conversion of hydrocarbons. According to the invention, at least one first gas containing at least 20% of oxygen by volume and a type of hydrocarbon are first all circulated in separate streams which are parallel to each other, without their being mixed, according to a spatial distribution such that the first gas is surrounded by the hydrocarbon; these substances are introduced into a mixing/reaction chamber at a first given circulation level, and while the substances are then allowed to mix, the oxygen and the hydrocarbon are ignited so as to give rise to the conversion reaction and then, at a second given circulation level situated downstream of the first, a quenching of the resultant mixture is performed in a chamber, the resultant quenched conversion products are recovered. The invention applies particularly to the manufacture of conversion products such as acetylene and ethylene.

9 Claims, 3 Drawing Sheets

APPARATUS FOR THE CONVERSION OF HYDROCARBONS

This application is a divisional of U.S. Ser. No. 07/278,521, filed Dec. 1, 1988 now U.S. Pat. No. 4,952,743 issued Aug. 28, 1990.

The present invention relates to a process and to an apparatus for the conversion of hydrocarbons such as methane, which are intended for the manufacture of conversion products such as acetylene.

The objective which is aimed at is, in fact, to convert hydrocarbon raw materials into basic products intended particularly for the chemical industry.

BACKGROUND OF THE INVENTION

Among the hydrocarbon raw materials or charges which may be chosen within the scope of the invention, there will be noted, besides methane, natural gases, liquefied petroleum gases (LPG), light gasolines and naphthas, heavy fractions of petroleum oil or those originating from its refining, crude oil and, more generally, gaseous and liquid hydrocarbons obtained either from fossil raw materials, schists and tar sands, coal, or from biomass, from matter of animal origin or from various wastes (household refuse, etc.).

As for the basic products which are obtained by conversion of these raw materials and which are at the present time widely employed in the chemical industry, these are either unsaturated hydrocarbons of low molecular weight, such as acetylene, olefins and diolefins, or saturated hydrocarbons, also of relatively low molecular weight, or else possibly carbon monoxide or hydrogen.

Various types of processes and of apparatus for converting hydrocarbons are in existence at present.

First of all, what are known as "thermal" processes may be mentioned. These processes may be divided into two large categories.

The first is that where the energy needed for the conversion reaction is contributed by a high-power electrical source (electric arc or plasma).

In the second category, the energy is of chemical origin and is obtained by the combustion of a part of the hydrocarbon charge itself (processes known by the name of "single-stage") or of another fuel, it being possible for the combustion products obtained to be then either mixed with the hydrocarbon (so-called "two-stage" processes), or used to heat refractory materials fitted to a wall of the reaction chamber, so as to ensure the conversion of this same hydrocarbon (so-called "cyclic" process).

The two essential characteristics of the known single-stage processes consist, on the one hand, in preheating the materials which are to be reacted (namely at least oxygen and a type of hydrocarbon) with the aid of an auxiliary combustion reaction and, on the other hand, in premixing these same materials before the exothermic oxidation reaction which will lead to the conversion of the initial hydrocarbon.

In these single-stage processes, the premixing of the materials, in a chamber provided for this purpose, is considered to be indispensable, the rate of diffusion of the gases being considered incompatible with the contact time of the materials with each other, which is necessarily limited to ensure the conversion reaction in appropriate conditions.

When the progress of reactions in a process of this type is examined more closely, it is noted that the hydrocarbon undergoes, partly, a conversion (to acetylene when methane is involved) and, partly, a conversion to carbon monoxide, hydrogen, carbon dioxide and water. Soot formation is unavoidable in practice and constitutes a disadvantage which is difficult to overcome. The necessary final quenching of the resultant reaction mixture makes it possible, when it is performed in oil, to recover a significant part of the sensible heat of the gases after reaction, while stabilizing the conversion products obtained. On the other hand, the selectivity (that is to say the percentage of hydrocarbons to be converted which are actually converted into the desired hydrocarbon conversion products) is rather mediocre, that is to say that a relatively high proportion of carbon monoxide is produced.

In two-stage processes, the first stage consists in producing a gas at a very high temperature by means of a combustion reaction of the hydrogen-oxygen type. Steam is generally added so as to moderate the temperature rise. In the second stage, the hot gas obtained is mixed with the hydrocarbon which is to be converted and which then undergoes a pyrolysis reaction leading to the pyrolysis products such as acetylene and ethylene in the case where methane has been taken as the initial hydrocarbon.

In general, in order to improve the mixing of the reactant products, the pyrolysis products obtained are circulated through a venturi tube or similar, after which they are quenched.

In practice, a process of this type appears, nevertheless, to be relatively poorly adapted, especially in the case where methane is employed as starting hydrocarbon. Furthermore, it has been found necessary for the walls of the apparatus in which the reaction takes place to be made of highly temperature-resistant materials (refractory materials) in view of the particularly exothermic and violent nature of the reaction.

SUMMARY OF THE INVENTION

The object of the invention is precisely to solve the difficulties and disadvantages of the various conversion processes which are known at present. This objective is achieved in the invention by providing for using as starting substance at least one type of hydrocarbon or of hydrocarbon charge, and a first gas which contains at least 20% of oxygen by volume.

first of all, causing these various substances to circulate in parallel streams and independently of each other, that is to say without mixing, while adopting a spatial distribution such that the first gas is surrounded on at least two sides by the said hydrocarbon, at a first given circulation stage, and while then allowing these substances to mix, igniting the oxygen and the hydrocarbon so as to induce the conversion reaction, then, as known per se and at a second given stage of circulation situated downstream of the first, quenching the resultant mixture by introducing into it a quenching fluid such as oil; whereupon the quenched conversion products will be recovered.

In certain cases, and especially in order to improve the selectivity of the reactions, it will nevertheless be advantageous to provide additionally, as a further starting substance, a second gas containing at least 30% of hydrogen by volume. This second gas will then be made to circulate, first of all without having mixed, in a parallel stream with the hydrocarbon and with the said first gas containing oxygen, this being substantially in mutual contiguity and, at the abovementioned stage of circulation where the hydrocarbon and the oxygen are ignited, while the substances are allowed to mix together, the hydrogen will also be ignited.

In this case, the substance obtained by the mixing and the combustion reaction of the oxygen-rich first gas and of the hydrogen-rich second gas will be mixed, as it were "as such", with the hydrocarbon which surrounds this second gas, without steam having first been added, before the substances are ignited.

Furthermore, in this case the reaction of the first gas will take place largely without contact with the hydrocarbon, as a result of the interposition of the second gas between the two.

It will also be noted that the mixing of the two gases and of the hydrocarbon will take place largely by means of diffusion, a characteristic which, as we have seen, has until now been considered to be ruled out.

It should be noted that, in the invention, the oxygen-rich first gas may contain a certain quantity of hydrogen. In practice, the quantity of hydrogen by volume which is present in the second gas will nevertheless be equal to at least 10% (preferably 100%) of the total quantity of hydrogen by volume present in the said first and second gases.

It will also be noted, insofar as the total quantities of hydrogen and oxygen by volume in the first and second gases present are concerned, that a hydrogen to oxygen ratio greater than 2/1, and preferably equal to 4/1, is advisable.

As already noted, the invention also relates to an apparatus for implementing the process which has just been outlined.

This apparatus, which is of the type comprising separate supply streams for the distribution of at least the oxygen-rich first gas and of the hydrocarbon charge, the said streams emerging into a mixing-reaction chamber in which the first gas and the said charge may be ignited by means of ignition and which is extended, at the opposite end to the place where the said streams emerge, by a quench chamber comprising conduits for recovering the conversion products, is characterized in that the said supply streams emerge into the mixing-/reaction chamber while extending substantially parallel to each other, with, from the inside outwards:

the stream in which the first gas circulates
then the stream in which the hydrocarbon charge circulates. If necessary, a hydrogen supply stream will be inserted between the oxygen and hydrocarbon supply streams. Also, a water supply stream may surround the hydrocarbon stream.

By virtue of this particular spatial distribution of the various substances, which ensures a decrease in the heat stresses in the apparatus, the walls of the mixing-reaction chamber may be made of metal. Understandably, this will result in the apparatus being easier and less costly to produce.

Furthermore, the risks inherent in its operation will be reduced when compared with existing equipment.

BRIEF DESCRIPTION OF THE DRAWINGS

The objectives, characteristics and advantages of the invention will become more clearly apparent from the description which is to follow, given with reference to the accompanying drawings in which.

DETAILED DESCRIPTION OF THE INVENTION

Figure 1:
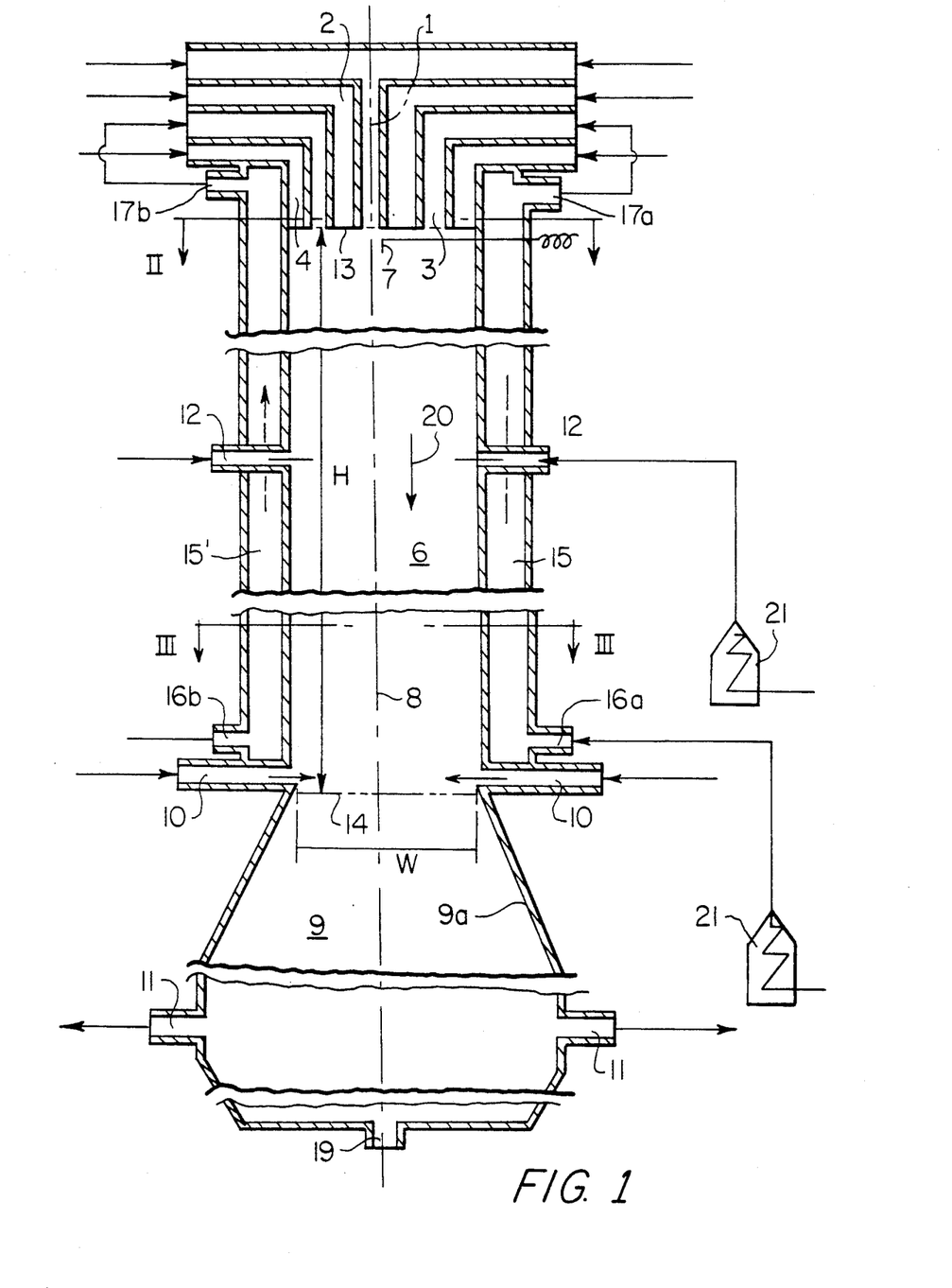
FIG. 1 is a partial view of the reactor in accordance with the invention, in a median cross-section along the line I—I of FIG. 5.
Figure 2:
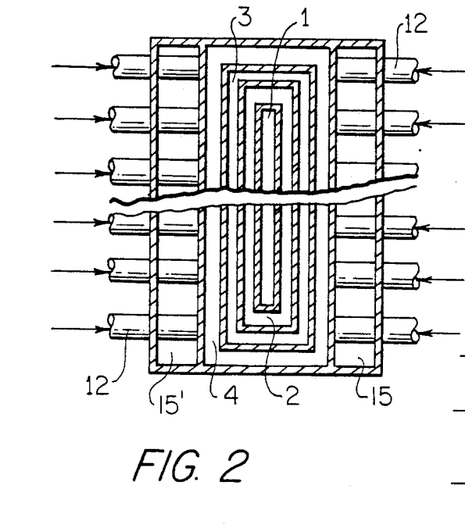
FIG. 2 is a view of the reactor feed conduits in section along the line II—II of FIG. 1.

With reference, first of all, to FIGS. 1 and 2, it can be seen that the reactor of the invention essentially comprises a mixing-reaction chamber 6 with a vertical general axis 8 which is extended in its axis and in its lower part by another chamber 9, known as a quench chamber, which is connected to the chamber 6 by means of a divergent funnel or distributor 9a.

In accordance with the invention, the mixing/reaction chamber 6 is fed at its top with at least one first gas containing at least 20% of oxygen and with a hydrocarbon charge, each emerging from a supply stream 1, 3 which are separated and arranged substantially parallel to each other, at least close to the spot where they open into the chamber in question.

Although this embodiment with two streams is wholly capable of being envisaged, it has not been illustrated as such. In fact, in the various figures it can be seen that, between the streams 1 and 3 a stream marked 2 is inserted, intended to feed the chamber 6 with a second gas containing at least 30% of hydrogen.

It can also be seen that around the feed stream 3 for the hydrocarbon charge to be converted a fourth stream marked 4 may be arranged. The purpose of this last stream is to feed the reactor with water, particularly in order to make it easier to maintain the wall temperatures of this chamber 6 at an acceptable level.

For the sake of clarity, the remainder of the description will be given with reference to this particular embodiment with four streams.

In accordance with the latter, the spatial distribution of the various reactor feeds, in the top part of the chamber 6, is therefore such that the streams extend substantially parallel to the reactor axis 8, one in another with, from the inside outwards stream 1, in which the oxygen-rich (at least 20%) first gas circulates
then stream 2 in which the hydrogen-rich (at least 30%) second gas circulates
then stream 3 in which the hydrocarbon charge to be converted circulates
then, although this is optional, the water feed stream 4.

In order to ignite the various substances which are allowed to enter the chamber 6 and thus to bring about the conversion operation, electrical means of ignition 7, supplied with a suitable high voltage, are provided near the upper part of this chamber.

Also visible near the intermediate part of this same chamber are channels or conduits 12 enabling an optional additional hydrocarbon charge, still to be discussed later, to be introduced substantially perpendicularly to the reactor axis 8. It will be noted, nevertheless, even at this stage, that this charge will be different in kind from that introduced via the stream 3.

In the lower part of chamber 6, nozzles 10 which emerge transversely to the axis 8 in the region of the junction between the chamber and the divergent funnel 9a, will be additionally responsible for feeding the quenching fluid such as, for example, oil.

Conduits 11 will subsequently enable the conversion products to be recovered and removed, after they have been quenched and hence stabilized. As is known per se, the quenching fluid, in its case, can be removed via the manifold 19.

Figure 4:
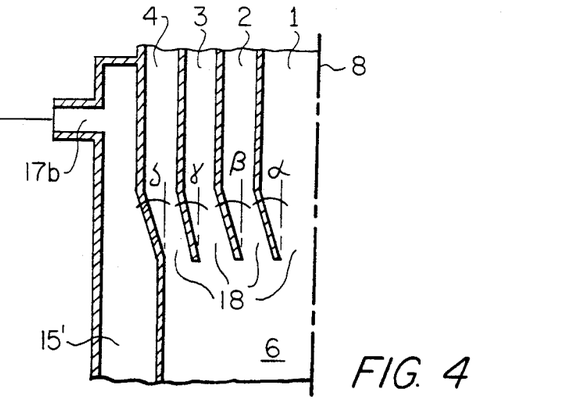
FIG. 4 is a possible form of embodiment of the end of the various abovementioned conduits, in the region where they emerge into the mixing reaction chamber, along a half-section along the plane of FIG. 1.

Furthermore, from FIG. 4 it will be seen that in the vicinity of the spot where they emerge into the chamber 6, the various streams may have an end part which gradually narrows down towards the chamber at a substantially constant angle, so as to form a neck or spout 18. In practice, the restriction angles $\alpha$, $\beta$, $\gamma$ and $\delta$ of the various streams will be adapted to the circulation conditions of the substances entering the reactor and to the operating conditions.

Figure 3:
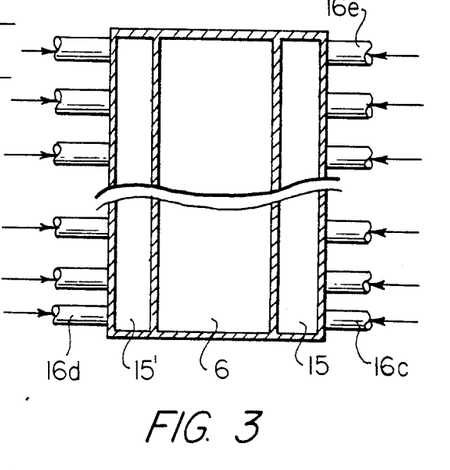
FIG. 3 is a view of the reactor in section along the line III—III of FIG. 1.
Figure 5:
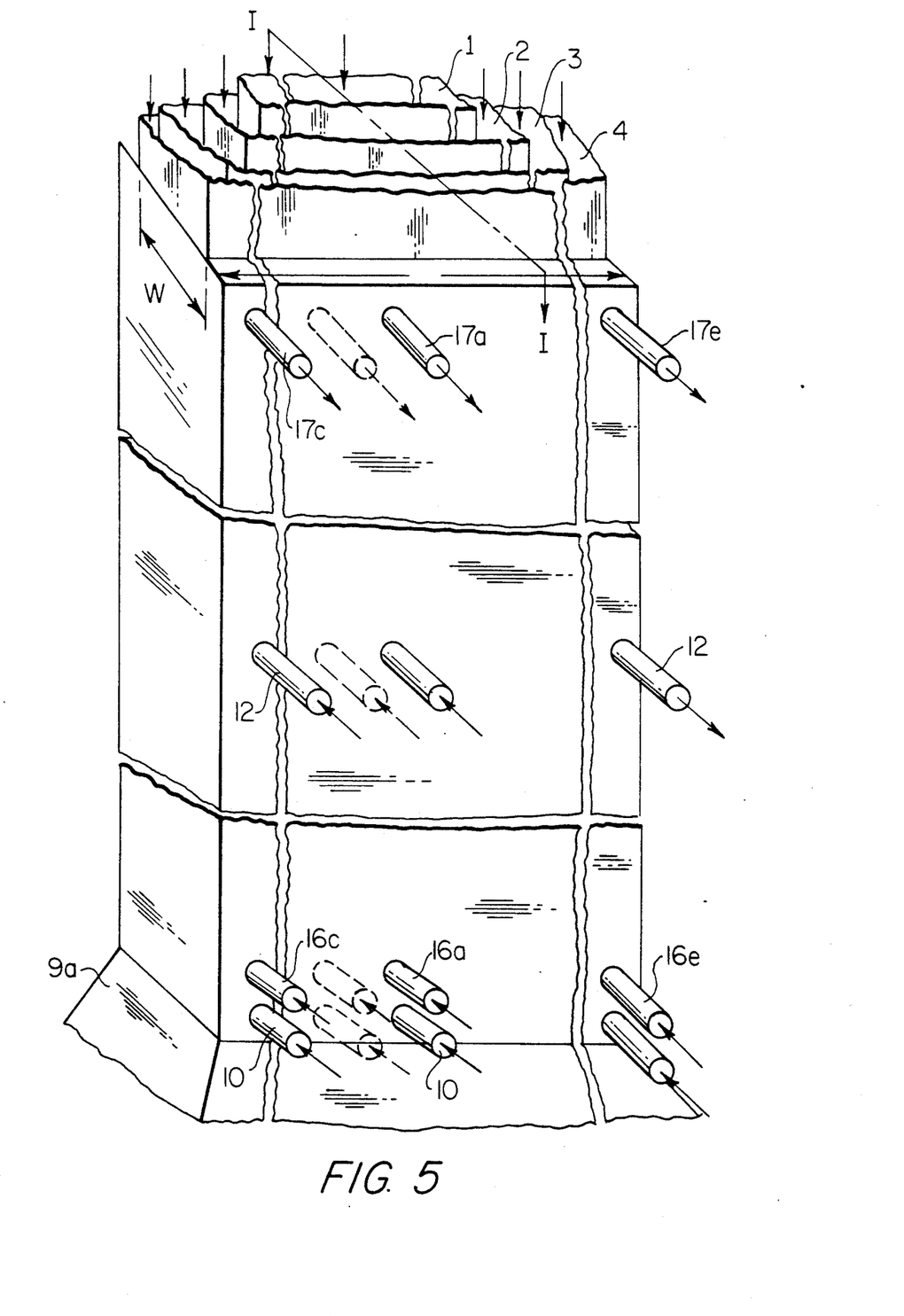
FIG. 5 is a diagrammatic external view of the apparatus of the invention.

Let us now turn more precisely to FIGS. 1, 3 and 5 to note the special shape and dimensions of the reactor of the invention and more particularly of the mixing/reaction chamber 6 of substantially cylindrical shape which has been illustrated with a rectangular section (FIG. 3). In FIG. 5, the reactor has not been shown to scale because, according to the invention, the ratio wetted surface/volume of the chamber 6 will be preferably between 40 and 250 $m^{-1}$ which corresponds to a value for W of 8-50.

By way of example, it will be possible to envisage a chamber of this kind with a width W of the order of 2 to $8 \times 10^{-2}$ m, a length L of the order of 8 to 10 m and a height H of approximately 4 to 5 m, this height being measured between an upper limit 13 of the chamber situated in the region where the supply streams emerge and a lower limit 14, in the region of which the chamber 6 is connected to the divergent funnel 9a. The ratio wetted surface $(2 \times H \times L)$/volume $(W \times H \times L)$ would then be approximately 100 $m^{-1}$.

In FIG. 1, it will also be noted that over most of its height and at least in parts, over its length L measured from the left wall to the right wall shown in FIG. 5, the chamber 6 may be surrounded by two preheating chambers 15, 15' so that all or some of the substances delivered via the streams 1-4 may be preheated by circulating countercurrentwise to the reacting substances, in contact with the hot peripheral wall of the chamber 6 (which, as will be seen, may be made of metal).

The hydrocarbon charge will be essentially the one preheated in this manner in practice. This charge, delivered via the stream 3, which is then independent of the other streams and which can be subdivided into a number of channels 16a, 16b etc., so as to distribute the charge flow over the length L of the chamber, will in this case be allowed to enter near the base of the preheating chambers 15, 15', and will then circulate freely over their height before being recovered via the channels 17a, 17b etc. which then recombine to form a single stream 3 again. Understandably, a preheating of this type would be implemented on the same lines in the case of substances other than the hydrocarbon charge. However, the preheating chambers 15, 15' would then need to be partitioned in order to prevent any mixing of the substances before they are introduced into the reactor.

Be that as it may, a preheating of this kind will promote the operating conditions of the reactor, whose method of operation will now be explained.

As already seen, after an optional preheating, the substances needed for the conversion reaction will first of all be allowed to enter the upper part of the mixing-/reaction chamber 6, into which they emerge in streams which are parallel to each other, in the direction of the arrow 20 with, going from the inside of the reactor outwards, the oxygen-rich first gas, then, surrounding it in a substantially contiguous manner, the hydrogen-rich second gas, itself surrounded, also in a substantially contiguous manner, by the hydrocarbon charge and, optionally, a stream of steam.

Near the entry of the mixing/reaction chamber 6 and while they are beginning to mix, these various substances are then ignited by the means of ignition 7, substantially at the same single given level of circulation, so as to trigger the conversion operation. A hydrogen/oxygen pilot flame (not shown) should make it possible in a convenient manner to ensure the continuity and control of this ignition.

Although they are difficult to state precisely and although they depend on the operating conditions, the hydrocarbon conversion temperatures should be between approximately 800° and 1600° C. in the top part of the chamber 6.

Be that as it may, the temperature of the walls of the chamber in question will be maintained generally below approximately 1100° C., for example by steam injection, by adapting the quantity of oxygen allowed to enter, or else by preheating the hydrocarbon to be converted in the chambers 15, 15'. The residence times of the substances in this chamber 6 will generally be between 2 ms and approximately 0.5 s and, preferably, between 10 and 100 ms.

Having entered the bottom part of the reactor, where the temperature will generally reach 200° to approximately 500° C., the conversion products will then be subjected, in the chamber 9 and according to a conventional method, to a quench in contact with the quenching fluid (such as oil) emerging from the nozzles 10, so as to reach substantially ambient temperature.

In the case where the type of hydrocarbon(s) which it is intended to convert does not consist essentially (that is to say to an extent of more than approximately 50%) of so-called "light" hydrocarbon(s), that is to say containing between two and five carbon atoms, it will be noted that in addition to this quenching, it may be found useful to provide a prequenching of the reaction mixture. A fluid or liquid "light" hydrocarbon charge of this kind will then be introduced via the channels 12 and will therefore emerge near the intermediate part of the chamber 6 and as a stream intersecting the reaction mixture.

It will be noted that when a hydrocarbon charge of relatively low molecular weight of this kind is employed, the quantity of hydrogen leaving the reactor will be increased.

Be that as it may, once they are stabilized by the quenching, the conversion hydrocarbons will be channelled into the bottom part of the chamber 9 and will be recovered via the discharge conduits 11 (see FIG. 1).

Let us now return briefly to the characteristics of the reactant substances employed, in order to note, first of all, that the oxygen-rich first gas which circulates in the central stream 1 of the reactor may optionally contain a certain quantity of hydrogen, while the hydrocarbon, in its case, may consist of a mixture of hydrocarbons and may also contain a certain quantity of steam (in this case at least approximately 10% by weight), or even of oxygen (in this case at least of the order of 5% by volume).

Nevertheless, it will be noted from now on that the quantity of hydrogen in circulation will in any case be in excess relative to the quantity of oxygen. More precisely, according to the invention, provision is made for the quantity of hydrogen by volume which is contributed by the first and second gases to be at least twice, and preferably four times, as great as the quantity of oxygen contributed by the first gas. Moreover, the quantity of hydrogen contributed by the second gas will represent at least 10%, and preferably 100%, of the total quantity of hydrogen contributed by the first and second gases.

In this way, hydrogen will act, in effect, as a "chemical" insulant between the oxygen-rich first gas and the hydrocarbon charge. Moreover, this excess hydrogen will be capable of intervening especially by promoting the dilution of the reacting substances and the control of the rise in temperature once the reactor is ignited.

It has also been observed that this intentional excess of hydrogen made it possible to improve the selectivity of the conversion of the initial hydrocarbon to be converted and therefore reduced the formation of soot and of other undesirable deposits, while promoting the formation of "less unsaturated" converted hydrocarbons (such as ethylene, propene etc.) at the expense of the "less saturated" converted hydrocarbons (such as acetylene).

Insofar as the free enthalpy needed for the conversion of these hydrocarbons is concerned, it will be noted that it is provided totally by the oxygen conveyed in the first gas and possibly in the hydrocarbon charge to be converted. In this latter case, it will be noted that the possibility which is offered of independently controlling the oxygen feeds provided by the streams 1 (oxygen-rich gas) and 3 (hydrocarbon), will offer an increased flexibility in the implementation of the process, as a function of the nature of the initial hydrocarbon charge and of the conversion products which it is desired to obtain. On this subject, it has been observed that the adjustment of the quantity of oxygen conveyed by the hydrocarbon affected the reaction temperatures, making it possible to adjust the quantity of carbon monoxide which is produced as well as the quantity of hydrogen leaving the reactor after the reaction and to obtain a truly "autothermal" operation of the process, that is to say such that all the substances enter the preheating chambers 15, 15' substantially at ambient temperature.

As can be seen, the process of the invention is clearly differentiated from the abovementioned single- or two-stage known conversion processes.

Should this point need to be explained further, it may be pointed out, in particular, that the oxygen present in the first gas is, in accordance with the chosen embodiment and at the time of the ignition of the substances in the mixing/reaction chamber 6, separated from the hydrocarbon charge by the hydrogen-rich second gas. A single-stage process characterized by the premixing of oxygen with the hydrocarbon before the ignition is therefore not involved in this case. Furthermore, in the invention, the gaseous substance resulting from the mixing and the combustion reaction between hydrogen and oxygen is mixed as it were "as such" with the hydrocarbon charge, without having been subjected to a preliminary addition of steam, as is the case in known two-stage processes.

Moreover, experiments which have been carried out have shown that, bearing in mind the geometry of the reactor and the ratio of the wetted surface to the volume of the mixing/reaction chamber of between 40 and 250 $m^{-1}$, the mixing of the substances as a whole took place largely by diffusion, a characteristic which has up to now been considered to be ruled out.

These same experiments have made it possible to demonstrate that the quantity of hydrogen leaving the reactor could be substantially the same as at the entry, which is wholly favorable in the sense that the hydrogen then would appear to be a true initiator or homogeneous "catalyst" of the conversion reactions of the hydrocarbon charge. In practice, the reactor will tend to operate in this manner proportionally to a greater degree as the quantity of oxygen contributed by the hydrocarbon stream is increased and as a preheating of all or part of the substances which are to react is performed. In practice, the ratio oxygen/hydrocarbon entering the reactor will be adapted essentially as a function of the degree of conversion (that is to say of the quantity of hydrocarbon converted over the quantity of hydrocarbon entering) and of the selectivity which are sought after.

Whatever the metering of these substances which is chosen, a preheating of this kind may, as has been seen, consist of a circulation, particularly of the hydrocarbon charge, countercurrentwise to the reacting substances, along the external walls of the mixing/reaction chamber 6, this heat transfer giving rise, as it were, to a first quenching (or cooling) of the reacting substances in the chamber.

However, in addition, a supplementary preheating, particularly of the abovementioned charge, may be envisaged, with the use of conventional exchangers such as 21, in which the substances to be preheated would circulate before reaching the reactor.

Be that as it may, it will be understood that the preheating by circulation along the thermal face of the walls of the chamber 6 will be largely promoted by the possible use of entirely metal walls (such as of 25 Cr/20 Ni or 25 Cr/35 Ni/1.5 Nb steel), in contrast to the known units whose walls are usually made of refractory materials.

Naturally, this possible metal construction of the reactor arises to a large extent from the fact that the highly exothermic reaction between oxygen and hydrogen takes place in the central region of the reactor, while the endothermic reaction of hydrocarbon conversion takes place in a peripheral region, close to the walls of the chamber 6, the hydrocarbon then acting as a heat insulator for the reactor wall. With regard to this thermal protection, it is quite obvious that it will be increased if steam (which may contain a small quantity of oil in dispersion) is circulated, emerging from the stream 4, along the internal face of the chamber walls.

It will be noted that this heat barrier could be improved even further by premixing water in the form of steam with the hydrocarbon charge circulating in the stream 3.

With regard to the usefulness of this steam present in the reaction mixture, whether it be that brought in from the outside by the feed streams or that produced in situ by the chemical reactions, it appears important to point out that it intervenes not only by affecting the temperatures and the partial pressures prevailing in the reactor, but also by reducing the soot deposits and by its beneficial oxidizing effect on the metal walls of this same reactor.

Although this has not been stated until now, nor illustrated, it is obvious that at the end of the quenching operation, after stabilization of the conversion products obtained, at least some of them may be recovered and recycled towards the corresponding entry streams.

On this subject, it is clear that the ways in which the products leaving the reactor (in particular hydrogen, carbon monoxide, the unconverted part of hydrocarbon(s)) are recycled are particularly flexible. More precisely, these recycling schemes may range from a first limiting case comprising, as is known per se, the separation of carbon monoxide and hydrogen from the recovered starting hydrocarbon, the conversion of this carbon monoxide into hydrogen, the recycling of the hydrogen into the stream 2 (and optionally 1) and of the hydrocarbon in question into the stream 3, to another limiting case where the carbon monoxide/hydrogen/-recovered starting hydrocarbon mixture is recycled as such, without fractionation, into the corresponding stream flows. Following the same line of thought, it would also be possible to fractionate, in accordance with a process which is known per se, a part of the hydrocarbons leaving the reactor in order to recycle them into the stream 3 and, if necessary, into the conduits 12.

A few operational examples will now be presented to clarify the application conditions of the invention as well as possible.

EXAMPLE 1

The streams 1, 2 and 3 are fed with oxygen, hydrogen and methane respectively.

The proportions by volume of these three gases are the following: 0.75/3/1.

The gases are preheated by being circulated at 15, 15' along the external wall of the mixing/reaction chamber of the reactor.

As they enter the chamber, ignition is initiated and the conversion reaction started. The methane conversion temperature in the mixing/reaction chamber is of the order of 1300° to 1400° C.

After quenching of the resultant reacting mixture, the following carbonaceous substances are obtained: acetylene, ethylene, ethane, carbon monoxide, carbon dioxide, as well as methane and hydrogen.

The average residence time of the substances in the reactor has been approximately forty milliseconds.

EXAMPLE 2

The operating procedure of Example 1 is repeated with the addition of oxygen to the methane, in a proportion of approximately 10% by volume.

An increased formation of unsaturated hydrocarbons (acetylene), of carbon monoxide and of hydrogen is then observed in comparison with Example 1.

EXAMPLE 3

The operating procedure of Example 1 is repeated and ethane is introduced in parallel via the channels 12 in a quantity which is substantially equal to that of methane.

An increase in the quantities of ethylene and of acetylene which are obtained, and also of hydrogen, is observed in comparison with the results of Example 1.

EXAMPLE 4

The operating procedure of Example 3 is repeated with ethane replaced by propane.

The formation of propene is observed in addition to the resultant products obtained in Example 3.

EXAMPLE 5

After a preheating of the hydrocarbon charge by circulation in the preheater-exchanger 21 and by heat exchange with the reactor walls (in chambers 15 and 15'), the following are introduced into the reaction chamber 6:
emerging from the stream 1: oxygen,
emerging from the stream 2: coke oven gas containing approximately 60% of hydrogen and 30% of methane, together with other hydrocarbons, carbon monoxide, carbon dioxide and nitrogen,
emerging from the stream 3: natural gas containing approximately 80% of methane, together with ethane, propane and butane.

In proportion, the volumetric quantities of the substances which circulate in the three streams are: 0.35/1/0.5.

After quenching, the reaction products obtained contain acetylene, ethylene, carbon monoxide and carbon dioxide, as well as small quantities of various monoolefins, diolefins, acetylenic compounds and saturated hydrocarbons.

EXAMPLE 6

The operating procedure of Example 5 is repeated with the coke oven gas replaced by so-called synthesis gas containing approximately 75% of hydrogen and 25% of carbon monoxide.

In proportion, the volumetric quantities of the substances which circulate in the three streams are 0.3/1/0.45 in this case.

After quenching, a gas mixture of the same kind as in Example 5 is obtained.

EXAMPLE 7

The following are introduced after being preheated by heat exchange with the reactor walls
via the stream 1, oxygen
via the stream 2, hydrogen
and via the stream 3, a mixture of steam and of hydrocarbons in a mass ratio equal to 0.65. The hydrocarbon charge consists in this case of a mixture of gas oil light ends and gas oil heavy ends. Its empirical formula is $CH_{1.86}S_{0.004}$. In proportion, the volumetric quantities of the various substances circulating in the three streams are 4/1/2.4
after quenching of the reacting mixture, a complex mixture is obtained of saturated hydrocarbons (including methane), unsaturated hydrocarbons (monoolefins, diolefins, acetylenic compounds), of benzene-related hydrocarbons, of carbon monoxide, of carbon dioxide, of sulphur dioxide and of hydrogen.

Although the above description has been given with reference essentially only to a particular embodiment, it should be clear that the invention is not limited solely to the latter. Various alternative forms of embodiment could be envisaged.

In particular, near the spot where they open into the mixing/reaction chamber 6, the various reactor feed streams could be arranged so that a given stream "surrounds" a more central stream only on two opposite sides, instead of surrounding it completely over its entire periphery, as illustrated, for example, in FIG. 2.

Furthermore, insofar as the reactor geometry is concerned, a substantially cylindrical annular mixing/reaction chamber 6 could be provided, fed by streams arranged coaxially according to a geometry which is also cylindrical annular.

Also, instead of an attached preheating by means of exchangers 21 situated upstream of the chambers 15, 15' (FIG. 1), it will be possible to arrange these same exchangers 21 just downstream, at the exit of the chambers in question.

Lastly, although it has been envisaged more particularly to manufacture the walls of the mixing/reaction chamber in metal, this does not in any case exclude the use of other materials and especially of "new" materials such as ceramics.

I claim:

1. A reactor for carrying out an exothermic conversion reaction by combustion of a first gaseous reactant with a second gaseous reactant, said reactor comprising:
    a mixing and reaction chamber for mixing and igniting therein said first and second reactants to carry out the exothermic combustion conversion reaction, said chamber being externally limited by an outer shell having walls made at least partially of heat conductive material selected from metal, metallic alloys and ceramics for transferring heat generated by the exothermic conversion reaction through said walls;
    ignition means for igniting said reactants in said mixing and reaction chamber and inducing said combustion conversion reaction;
    a first feed conduit means communicating with said mixing and reaction chamber for introducing said first reactant to one end thereof;
    a second feed conduit means communicating with said mixing and reaction chamber for introducing said second reactant to said one end thereof, said second feed conduit means extending externally along said first feed conduit means and extending substantially parallel to and substantially concentric with said first feed conduit means at least adjacent to said mixing and reaction chamber;
    discharge conduits in communication with said mixing and reaction chamber for discharging outside the reactor products of said conversion reaction; and,
    a plurality of preheating chambers communicating separately and respectively with a respective one of said first and second feed conduit means and being supplied with at least one of said reactants, said preheating chambers extending externally about and along said outer walls of the mixing and reaction chamber for preheating said at least one reactant and for providing said mixing and reaction chamber with a first inner quenching zone extending along said preheating chambers by transferring heat from said mixing and reaction chamber to said at least one reactant circulating in said preheating chambers, before supplying said at least one reactant to said at least one of said first and second feed conduit means.

2. A reactor according to claim 1 wherein said discharge conduits are located at a lower end of said mixing and reaction chamber, said reactor further comprising nozzles for supplying said mixing and reaction chamber with a quenching fluid and providing said mixing and reaction chamber with a second quenching zone situated between said first quenching zone there below and said discharge conduits for supplementarily quenching said reaction products before their discharge.

3. A reactor according to claim 1 wherein said mixing and reaction chamber has substantially a rectangular section and a ratio of wetted wall surface (2H×L) to volume (H×L×W) between about 40 and about 250 m$^1$.

4. A reactor for converting hydrocarbon raw materials into conversion products by inducing at least an exothermic combustion conversion reaction, comprising:
    a mixing and reaction chamber for carrying out the combustion reaction, said chamber being externally limited by an outer shell having walls made at least partially of heat conductive material selected from metal, metallic alloys and ceramics for transferring heat generated by the exothermic combustion conversion reaction through said walls;
    at least three distinct feed conduit means for separately feeding three reactants comprising hydrocarbon raw material to an end of said mixing and reaction chamber, said reactants to be mixed and reacted together in said mixing and reaction chamber, said at least three feed conduit means extending substantially parallel to and substantially concentric with each other at least adjacent to said mixing and reaction chamber and comprising, from the innermost conduit means to the outermost conduit means, a first feed conduit means, a second feed conduit means extending along said first conduit means, and a third feed conduit means extending along said second conduit means;
    ignition means for igniting said reactants within said mixing and reaction chamber, inducing said combustion conversion reaction;
    discharge conduits communicating with said mixing and reaction chamber for discharging outside the reactor conversion products;
    a plurality of preheating chambers communicating separately and respectively with a respective one of said three distinct feed conduit means and being supplied individually with one of said reactants before said reactant feeds a corresponding conduit means, said preheating chambers extending externally about and along said outer walls of the mixing and reaction chamber in contact therewith for providing said mixing and reaction chamber with a first inner quenching zone extending along said preheating chambers, together with a preheating of said reactants in said preheating chambers, by transferring heat thereto from said mixing and reaction chamber through said outer walls of the mixing and reaction chamber.

5. A reactor according to claim 4 wherein said discharge conduits are located at a lower end of said mixing and reaction chamber, said reactor further comprising nozzles for supplying said mixing and reaction chamber with a quenching fluid and providing said mixing and reaction chamber with a second quenching zone there below situated between said first quenching zone and said discharge conduits for a supplementary quenching of said reaction products, before their discharge.

6. A reactor according to claim 4 in which a fourth feed conduit is provided, said fourth feed conduit extending along said third feed conduit on at least two opposite outer sides thereof for introducing steam into said mixing and reaction chamber.

7. A reactor according to claim 4 wherein said mixing and reaction chamber has a ratio of wetted wall surface ($2H \times L$) to volume ($H \times L \times W$) between about 40 and about 250 m$^1$.

8. A reactor according to claim 4 wherein said mixing and reaction chamber has a substantially rectangular vertical cross section and the shortest distance in said vertical cross section between two opposite outer walls of said mixing and reaction chamber is between about 8 mm and 50 mm.

9. A reactor according to claim 5 further comprising additional conduits for introducing hydrocarbon feed into said mixing and reaction chamber substantially at right angles to side walls of said mixing and reaction chamber and in a region of said mixing and reaction chamber which is intermediate between a zone where said at least three feed conduits communicate with said chamber and said second quenching zone thereof.

* * * * *